United States Patent [19]

Raleigh et al.

[11] 4,118,194
[45] Oct. 3, 1978

[54] SENSOR FOR FLUID COMPONENTS

[75] Inventors: Douglas O. Raleigh, Encino; Leo E. Topol, Canoga Park, both of Calif.

[73] Assignee: Rockwell International Corporation, El Segundo, Calif.

[21] Appl. No.: 785,988

[22] Filed: Apr. 8, 1977

[51] Int. Cl.² .................. G01N 27/26; G01N 27/40; H01M 4/00
[52] U.S. Cl. .................. 422/98; 23/230 R; 23/232 E; 204/195 R; 204/1 T; 429/90; 429/101; 429/191
[58] Field of Search .......... 23/254 E, 230 R, 232 E; 429/90, 101, 191; 204/1 N, 195 R

[56] References Cited

U.S. PATENT DOCUMENTS

| | | | |
|---|---|---|---|
| 2,851,411 | 9/1958 | Bly | 429/90 X |
| 3,258,759 | 6/1966 | Bernstein | 429/90 X |
| 3,763,025 | 10/1973 | Chand | 204/1 N |
| 3,764,269 | 10/1973 | Oldham | 23/254 E |
| 3,840,407 | 10/1974 | Yao | 429/101 X |
| 3,880,722 | 4/1975 | Beltzer | 23/254 E X |
| 3,909,204 | 9/1975 | Allen | 23/254 E |
| 3,970,431 | 7/1976 | Wise | 23/254 E |
| 4,001,756 | 1/1977 | Heijne | 23/25 E X |
| 4,007,096 | 2/1977 | Jasinski | 204/1 N |
| 4,029,854 | 6/1977 | Walsch | 429/101 X |
| 4,052,268 | 10/1977 | Blurton | 204/1 N |

*Primary Examiner*—Sidney Marantz
*Attorney, Agent, or Firm*—L. Lee Humphries; Henry Kolin; Clark E. DeLarvin

[57] ABSTRACT

An electrochemical device for sensing fluid components, particularly gases, comprises a composition with which the component reacts to liberate elemental chlorine, bromine, fluorine or iodine. The chlorine, bromine, fluorine or iodine passes through a particulate layer of vitreous carbon and activates the positive electrode of a solid ionic electrolyte battery of the type: halogen/solid ionic electrolyte/metal electrode, whereby a voltage is generated across a measuring device, the voltage being a known measure of the concentration of the fluid component.

11 Claims, 2 Drawing Figures

SENSOR FOR FLUID COMPONENTS

BACKGROUND OF THE INVENTION

The present invention relates to an electrochemical device, for sensing fluid components and particularly gases, which utilizes a solid ionic electrolyte. Prior art fluid component sensors, e.g., polarographic oxygen sensors, typically use an electrolytic cell having two electrodes separated by a liquid electrolyte. One of the electrodes and/or the electrolyte is exposed through a permeable membrane to the oxygen to be assayed. The disadvantages of these cells are their bulk and inability to function at temperatures which would ordinarily evaporate or freeze the solution.

More recently, in U.S. Pat. No. 3,764,269 there is suggested an improved sensor for fluid components. The disclosed sensor comprises a thin membrane through which the component passes to react with a composition to liberate elemental chlorine, bromine, fluorine or iodine. The chlorine, bromine, fluorine or iodine passes through a porous graphite layer and activates the positive electrode of a solid ionic electrolyte battery of the type: halogen/solid ionic electrolyte/metal electrode, whereby a current flow is generated through a measuring device, the current being proportional to the concentration of the fluid component.

The suggested device overcame many of the problems of prior art sensors in that it was compact and could be operated over a wide range of temperatures. Nonetheless, such a device is not without need of improvement. More particularly, the current generated by such a device is of very low magnitude and requires a highly sensitive current measuring device or the use of some external means for amplifying the magnitude of current flow such that it is more readily readable with commercially available instrumentation. In addition, the response time of the suggested device is substantially slower than is desirable. Another disadvantage of such a device is that it has been found that it is relatively unstable with respect to time and to obtain accurate measurements it must be calibrated at least daily when in constant use.

SUMMARY OF THE INVENTION

In accordance with the present invention there is provided an improved sensor for fluid components of the type which utilizes a solid ionic electrolyte battery. Broadly, the present invention comprises a first means including a composition reactive with at least one component of the fluid to liberate an elemental halogen selected from the group consisting of chlorine, bromine, fluorine or iodine upon exposure to said component; a porous matrix electrode comprising a particulate layer of vitreous carbon in cooperative relation to said first means forming a first electrode through which liberated chlorine, bromine, and fluorine or iodine pass; and a solid electrolyte cell with a voltage measuring means across its electrodes. The cell includes the porous matrix electrode and the measuring means operatively associated with said matrix and responsive to liberated halogen for measuring a voltage. The voltage measures the gas phase concentration of the chlorine, bromine, fluorine or iodine produced, which concentration is stoichiometrically related in a known way to the concentration of the component in the fluid.

In accordance with the present invention it has been found that the response time of the device is substantially improved through the use of particulate vitreous carbon or platinum powder. However, carbon is particularly preferred in view of its faster response time and significantly lower cost. It is essential, however, that the vitreous carbon have a particle size of less than about 500 microns and preferably less than about 100 microns. When particulate vitreous carbon is used for any given concentration of a component in a fluid stream, the present device has a response time which is faster than that of the device disclosed in U.S. Pat. No. 3,764,269 by a factor of from about 1.2 to 2. Another advantage of the present invention is that it gives accurate stable readings over extended periods of time by virtue of using a potentiometric measurement as opposed to measuring current. Specifically, in the device disclosed in the aforesaid patent, it has been found that with a constant concentration of a component, the curret output of the device can decrease by a factor of 2 or more in several days and continues to decline thereafter. Hence, such a device requires frequent calibration to obtain accurate indications of the concentration of the component. In contrast, the voltage output of the present invention is stable for extended periods of time and requires no calibration.

In a particularly preferred embodiment of the present invention there is provided a device for sensing the $NO_2$ concentration of a gaseous stream in which the device comprises a first means including lead iodide to react with said $NO_2$ and liberate elemental iodine; a porous matrix electrode comprising a particulate layer of vitreous carbon in cooperative relation to said first means, and forming the first electrode through which said liberated iodine passes, said porous matrix electrode being in a spaced relation to said first means; and a solid electrolyte cell with a voltage measuring means across its electrodes, including said porous matrix electrode, a silver iodide solid ionic electrolyte, and a silver electrode, said measuring means being operably associated with said matrix and responsive to said liberated iodine for measuring a voltage which is correlatable to the gas phase concentration of said iodine, said gas phase concentration being equal to the concentration of $NO_2$ in said gaseous stream.

It is, therefore, an object of the present invention to provide an accurate sensing device, for substances in a fluid medium, which is operable at high temperatures and requires no calibration.

It is a further object of the present invention to provide a solid state sensing device for substances in or components of a fluid medium which is stable for extended periods of time.

It is another object of the present invention to provide a solid-state gas component sensing device which produces a readily measurable voltage which is a measure of the component concentration in a static or flowing gas under examination.

BRIEF DESCRIPTION OF THE DRAWINGS

These and other objects of the present invention will become more apparent from the following detailed description of the preferred embodiment of the present invention taken together with the drawings wherein.

DETAILED DESCRIPTION OF THE INVENTION

Figure 1:
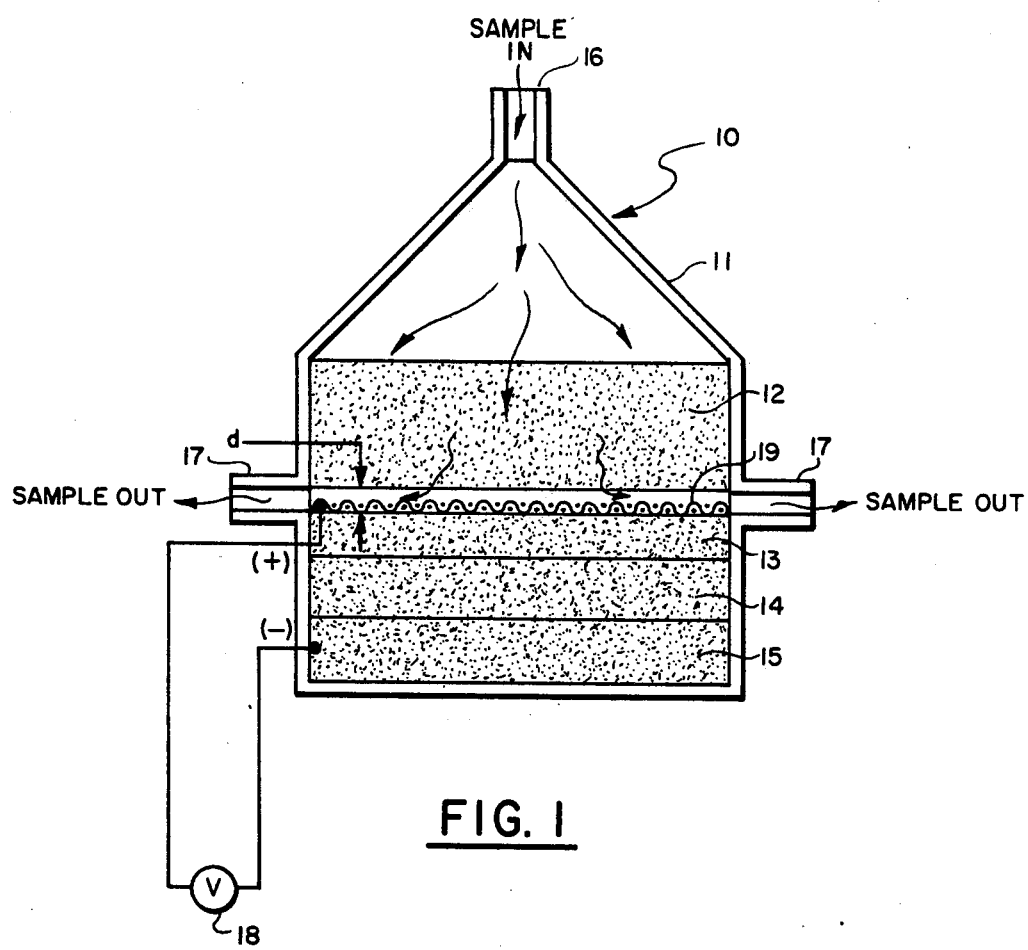
FIG. 1 is a sectional view of a preferred embodiment.

Referring now to the drawing in detail, a preferred embodiment of the device 10 for sensing at least one component of fluid substance comprises a housing 11, which contains a layer 12 of a halogenic compound from which a halogen is liberated upon exposure to certain reactive gases. Layer 12 has an open structure in the form of a loose powder or other physical structure which allows liberated gaseous halogen to pass through to an electrode 13, which is in cooperative relation with layer 12. Electrode 13 may be adjacent or abutting layer 12, or it may be in spaced relation $d$ therefrom. The dimension $d$ may be any practical value, but particularly good response times are obtained when dimension $d$ is no greater than several millimeters, for example, from about 0 to 5 millimeters and preferably from about 1 to 3 millimeters.

In accordance with the present invention, electrode 13 comprises a thin inert layer of particulate vitreous carbon having a median particle size of less than about 500 microns and preferably less than about 100 microns. Particularly good results are obtained when the median particle size is within the range of from about 10 to 100 microns. Electrode 13 is in contact with, and preferably partially imbedded in a solid ionic electrolyte 14. Electrolyte 14 has an opposite side, which has a contacting interface with a metal electrode 15. The preferred electrode is comprised of a mixture of graphite, ionic electrolyte and powdered silver. It will be appreciated any electrode consisting of metallic silver or having metallic silver as a component could be used, however, the powdered silver electrode is preferred over, for example, a solid silver electrode, since it provides better electrical contact with the solid ionic electrolyte 14.

The device further includes an electrical potential measuring means 18, which is electrically connected to vitreous carbon electrode 13 and the metal electrode 15 for measuring an electrical potential generated between the halogen and the metal electrode. In a preferred embodiment of the invention, the device further includes a platinum screen 19, which acts as an electrical connector and also serves to retain the particulate vitreous carbon electrode 13 in place when dimension d is greater than zero.

It is of particular advantage of the present invention that measuring means 18 need not be a highly sensitive device, since the potential generated will be within the range of from about 0.1 to 1.0 volts, and generally within the range of from about 0.3 to 0.5 volts. Thus, potential measuring means 18 may be any of the commercially available high impedance potentiometers encompassing the aforesaid range, with a readability of about 0.001 volt being sufficient to detect changes in the concentration of the component of interest, as low as several hundredths of a ppm.

In operation, a fluid sample is introduced into the device 10 through an inlet 16 and passes through halogenic composition 12, across the face of the vitreous carbon electrode 13 and exits through outlets 17. The reactive component of the gas reacts with halogenic composition 12 to liberate elemental halogen, which activates the electrochemical cell generating an electrical potential between vitreous carbon electrode 13 and metal electrode 15, which is measured by potential measuring means 18. This potential is a direct measure of the concentration of the component in the gas stream, via the application of the well-known Nernst Law in classical electrochemistry, the known standard free energy of the electrochemical cell reaction, and the known stoichiometry of the iodine-releasing reaction. Suitable halogenic compositions for use in the present invention are those compositions which liberate a halogen upon exposure to a reactive component of interest. Lead iodide, for example, is a preferred iodogenic compound from which iodine is liberated upon exposure to certain reactive gases, e.g., nitrogen dioxide, in the preferred embodiment. A particular advantage of lead iodide is that it will not react with other gases such as oxygen, carbon dioxide, nitric oxide, and sulfur dioxide at the normal operating temperature of the device. Thus, this embodiment is particularly useful for monitoring the nitrogen dioxide content of ambient air, which will, of course, contain oxygen and carbon dioxide, and may contain significant amounts of sulfur dioxide and nitric oxide. While lead iodide is preferred, a number of different types of halogen liberating compositions also may be utilized for different applications in accordance with the present invention.

With respect to iodine liberating compositions, one type is an iodine-containing composition which yields elemental iodine by replacement upon exposure to a reactive fluid substance. Thus, certain iodides, such as aluminum iodide, yield iodine in response to a variety of oxidizing agents including atmospheric oxygen in accordance with reactions such as:

$$4AlI_3 + 3O_2 \rightarrow 2Al_2O_3 + 6I_2.$$

Others, such as lead iodide and potassium iodide, require more energetic oxidizing agents in order to yield iodine at a rate sufficient to activate the electrochemical cell, e.g., $$PbI_2 + NO_2 \rightarrow PbO + I_2 + NO$$

$$2KI + F_2 \rightarrow 2KF + I_2.$$

Still others require special conditions to liberate iodine in the presence of an oxidizing agent. For example, iodoform, $CHI_3$ reacts with air to produce iodine at a rate sufficient to activate the electrochemical cell only in the presence of sunlight. A device utilizing iodoform could also be utilized as a light sensing element or a combined air-light sensor.

A second type of iodine liberating compounds are compounds in which iodine fills an electropositive role, such as iodine pentoxide. This compound reacts with a reducing agent to produce the requisite elemental iodine in accordance with reactions of which the following is an example:

$$I_2O_5 + 5CO \rightarrow I_2 + 5CO_2.$$

A third type of iodogenic compositions are those compositions which comprise a salt plus an oxidizing agent. Iodides react with many proton donors, e.g., hydrogen chloride, to produce hydrogen iodide by a replacement reaction:

$$I^- + HCl \rightleftharpoons Cl^- + HI.$$

A variety of oxidizing agents will convert the hydrogen iodide to iodine, displacing the above equilibrium and leading to a stoichiometric conversion to iodine. Potassium iodide plus manganese dioxide, for example, reacts with hydrogen chloride in the following manner:

$$KI + HCl \rightarrow KCl + HI$$

$$4HI + MnO_2 \rightarrow MnI_2 + 2H_2O + I_2$$

The oxidizing agent could also contribute additional iodine if, for example, potassium iodate were used.

A fourth type of iodogenic compositions are those compositions which comprise a salt plus oxidizing agent plus potential proton donor. Thus, compositions of the third type, including a potential proton source within the iodogenic mixture, are contemplated. Water is not a sufficiently good proton donor to liberate iodine from an iodide-iodate mixture. However, in the presence of substances which dissolve in or react with water or other solvent to yield acidic solutions, proton donation becomes possible. An example of this class are the double salts $2NaIO_3.3NaI.15H_2O$ and $2NaIO_3.3NaI.20H_2O$. These compositions in the presence of nitrogen dioxide decompose in the following manner:

$$2NO_2 + 3H_2O \rightarrow NO_3^- + NO_2^- + 2H_3O+$$

$$H_3O+ + I^- \xrightarrow{-HI + H_2O},$$

$$6HI + IO_3^- \rightarrow I^- + 3H_2O + 3I_2.$$

In addition to the above salts, mixtures of the individual hydrates $NaIO_3.H_2O$ and $NaI.2H_2O$ also react similarly. Further, mixtures of $NaIO_3$, $NaI$ and $H_2O$, which are dried carefully, also behave as above. As long as no excess moisture is present, these solid salts do not react with $CO_2$, CO or hydrocarbons.

Table I exemplifies the various embodiments of the present invention as applied to iodogenic compounds and identifies the reactive fluid substance which is detected.

Several iodogenic agents are specific to certain fluid components. Solid sodium iodate monohydrate ($NaIO_3.H_2O$) reacts readily at room temperature with sulfur dioxide releasing iodine. This salt will not yield iodine by reaction with other gases such as oxygen and chlorine.

$$NaIO_3.H_2O + SO_2 \rightarrow NaIO_3 + H_2SO_3$$

$$NaIO_3 + 3H_2SO_3 \rightarrow NaI + 3H_2SO_4$$

$$NaIO_3 + 5NaI + 6HSO_4^- \rightarrow 3I_2 + 3H_2O + 6SO_4^{--} + 6Na+.$$

For detecting ozone in the presence of other gases such as sulfur dioxide and hydrogen chloride, solid mercuric iodide ($HGI_2$) can be used to yield iodine in a room temperature reaction. Solid copper iodide (CuI) has been found to be a specific detectant for nitrogen oxides and will react readily with $NO_2$ and NO at room temperature to yield iodine.

With respect to chlorine and bromine, there are many chlorogenic and bromogenic compounds which act in an analogous manner to the above iodogenic compounds in sensing fluid components. For example, bromides such as aluminum bromide ($AlBr_3$), boron bromide ($BBr_3$) and beryllium bromide ($BeBr_2$), will yield elemental bromine in response to a variety of oxidizing agents such as atmospheric oxygen and chlorine. Other bromides and some chlorides require more energetic oxidizing agents in order to yield elemental bromine or chlorine at a rate sufficient to activate the electrochemical cell. For example, potassium bromide (KBr) yields elemental bromine by reaction with chlorine or fluorine and potassium chloride (KCl) yields elemental chlorine by reaction with fluorine. An illustration of the compositions which comprise a salt and and oxidizing agent is potassium bromide plus manganese dioxide which reacts with hydrogen chloride to yield elemental bromine. With respect to compositions which comprise a salt plus oxidizing agent plus potential proton donor, bromide (e.g., NaBr)-bromate (e.g., $NaBrO_3$) water mixtures and chloride (e.g., NaCl)-chlorate (e.g., $NaClO_3$) water mixtures can be used as well as the above described iodide-iodate mixtures for reaction with acid gases in the presence of a proton donor. With respect to chlorine, solid oxides such as lead dioxide ($PbO_2$) and manganese dioxide ($MNO_2$) and other solid oxidizing agents such as potassium chlorate ($KClO_3$) react readily with hydrogen chloride at room temperature to yield chlorine which can be detected by a solid state electrochemical cell as disclosed herein. These oxides are specific to hydrogen chloride and will not react with other gases such as oxygen or nitrogen dioxide. Rather than detecting the released chlorine directly, it can be reacted with another salt such as mercuric bromide or iodide ($HGI_2$) to yield bromine or iodine which is then detected by the electrochemical cell.

A fluid component such as ozone can react with various fluorine-containing compounds to yield detectable elemental fluorine. Such compounds would include fluorides of lanthanum III, aluminum III, cerium III, chromium III, gadolinium III, Nd III, Pr III, Sm III, Sc III, Tb III, Ti III, vanadium V and Y III. Aluminum

TABLE I

| Iodogenic Compound | Reactive Component | Not Reactive To |
|---|---|---|
| $AlI_3$ | | |
| $BI_3$ | $O_2$, $Cl_2$ and other | Non-oxidizing |
| $BeI_2$ | oxidizing gases | gases |
| $PbI_2$ | $NO_2$ | $O_2$, $SO_2$, NO and $CO_2$ |
| KI | $F_2$, $Cl_2$, $O_3$ | $O_2$ |
| $I_2O_5$ | CO, NO, $C_2H_2$, $NH_3$ | $SO_2$, $N_2O_4$ |
| KI + $MnO_2$ | HCl and other protonic acid gases* | Dry $SO_2$, $N_2O_4$, $O_2$ |
| $2NaIO_3 . 3NaI . 15H_2O$ | All acid gases*: | |
| $2NaIO_3 . 2NaI . 20H_2O$ | $SO_2$, $N_2O_4$, $NO_2$, NO, $Cl_2$ | |
| $CHI_3$ | Air in sunlight | Air in the dark |

*Acid gases are those which dissolve in or react with water or other solvent to yield acidic solutions.

Other hydrated iodates as well as double salts such as $Pb(IO_3)_4.2HIO_3.2H_2O$ will also react with sulfur dioxide to release iodine. The reactions involved with sodium iodate monohydrate are believed to be:

and yttrium are preferred based on thermodynamic data.

It is also within the purview of the present invention to utilize combinations of sensor cells, each with its upstream halogenic layer, where one or more reactive fluids are to be detected. In this manner, for instance, the concentration of a reactive fluid B may be measured by difference, using individual cells that detect A and (A+B). Other similar modifications contemplated are the use of inert materials with the halogenic compounds and the dilution of said compounds with other active materials, such as drying agents, to enhance the desired reactive process. The term halogenic includes not only chlorogenic, bromogenic, fluorogenic and iodogenic compounds, but the so-called halogenoids, for example, potassium cyanide (KCN) and potassium thiocyanate (KSCN).

The solid ionic electrolyte 14 of the preferred embodiment is silver iodide. However, a number of compounds, including $RbAg_4I_5$, silver bromide and silver chloride, may be used, so long as the halide solid electrolyte in contact with the vitreous carbon electrode corresponds to the halogen to be detected. Thus, silver iodide-based compositions should be employed to detect released iodine. A wide variety of systems using solid ionic electrolytes are disclosed in the applications of Argue et al, entitled "Solid Ionic Conductors," now U.S. Pat. No. 3,519,404, and Boone B. Owens, "Solid State Electrochemical Device," U.S. Pat. No. 3,476,606, the disclosures of which are incorporated herein by reference.

The opposite side of the layer of solid electrolyte 14 has a contacting interface with a metal electrode 15. For the solid ionic electrolytes the peferred electrode is comprised of a mixture of graphite, ionic electrolyte, and powdered silver, although any electrode consisting of metallic silver or having metallic silver as a component could be used. The powdered silver electrode 15 is preferred instead of a solid silver electrode because it provides better electrical contact with ionic electrolyte 14, however, solid silver could be used for electrode 15 with a slight decrease in stability. The silver containing electrode 15 is electrically connected to the particulate vitreous carbon electrode 13, through a potential measuring device 18, which registers the electron exchange taking place in the following chemical reactions:

At the interface of the electrode 13 and the electrolyte 14: $Cl_2$, $Br_2$ or $I_2 + 2e^- \rightarrow 2Cl^-$, $2Br^-$ or $2I^-$; and at the interface of the electrolyte 14 and the silver containing electrode 15: $2Ag \rightarrow 2Ag^+ + 2E^-$.

Thus, the silver electrode 15 provides silver ions and electrons which contribute to the electrical potential across measuring device 18. Measuring device 18 measures a voltage which represents the concentration of free chlorine, bromine or iodine from the chlorine-, bromine- or iodine-furnishing layer 12. This concentration is a known stoichiometric fraction or multiple of the concentration of the reactive component in the fluid substance which passes through the device 10.

EXAMPLE

The following example demonstrates the advantages of a device constructed in accordance with the present invention. In the particularly preferred embodiment, the device is for sensing $NO_2$ in air and is substantially as depicted in FIG. 1, wherein housing 11 is a Pyrex glass or Teflon container. The layer of halogenic compound 12 is a thin layer of particulate lead iodide having about a 0.7 cm thickness. The porous electrode 13 is a layer of vitreous carbon particles having a median particle size of less than 50 microns and a thickness less than 1.0 mm, having one surface spaced about 0.3 cm from the reactive lead iodide layer 12 and the other surface contacting and partially impregnated in one face of the solid ionic electrolytic layer 14. The layer 14 comprises a ¼ cm thick layer of silver iodide and has one surface operatively contacting a powdered silver electrode 15, which is about 0.3 cm in thickness. A voltage measuring means 18 is connected between the two electrodes 13 and 15. The measuring means 18 is a commercially purchased, solid-state, high impedance digital readout voltmeter capable of measuring potentials within the range of from 0.1 to 1.0 v with a 1.0 mv resolution.

All the layers in the preferred embodiment are circular in cross section and have a radius of about 0.63 cm. In order to ensure proper control of the exposure to the environment, the housing 11 is provided with closure means (not shown) such as valves, to keep out oxygen or other reactive fluid components and thus prolong the life of the sensor when it is not in use. The preferred embodiment has a life of the order of several months, assuming continuous exposure to the normal $NO_2$ content of the air. Its response time is substantially less than one minute for $NO_2$ concentrations greater than 1ppm. The longevity of the device is primarily a function of the thickness of layer 12, because when it is completely reacted the device will cease to function. The life is longer for a thicker layer. The thickness of reactive layer 12 affects the time required for the liberated gaseous chloride, bromine or iodine to diffuse through to vitreous carbon layer 13, and hence the response time of the device. Thus, it preferably is made just thin enough to permit the iodine, or the chlorine or bromine, to reach a diffusion rate equal to the rate at which it is produced within a time of a minute or so; the rate of production of the chlorine, bromine or iodine being proportional to the product of the concentration of the component in the sample and the sample flow rate.

Figure 2:
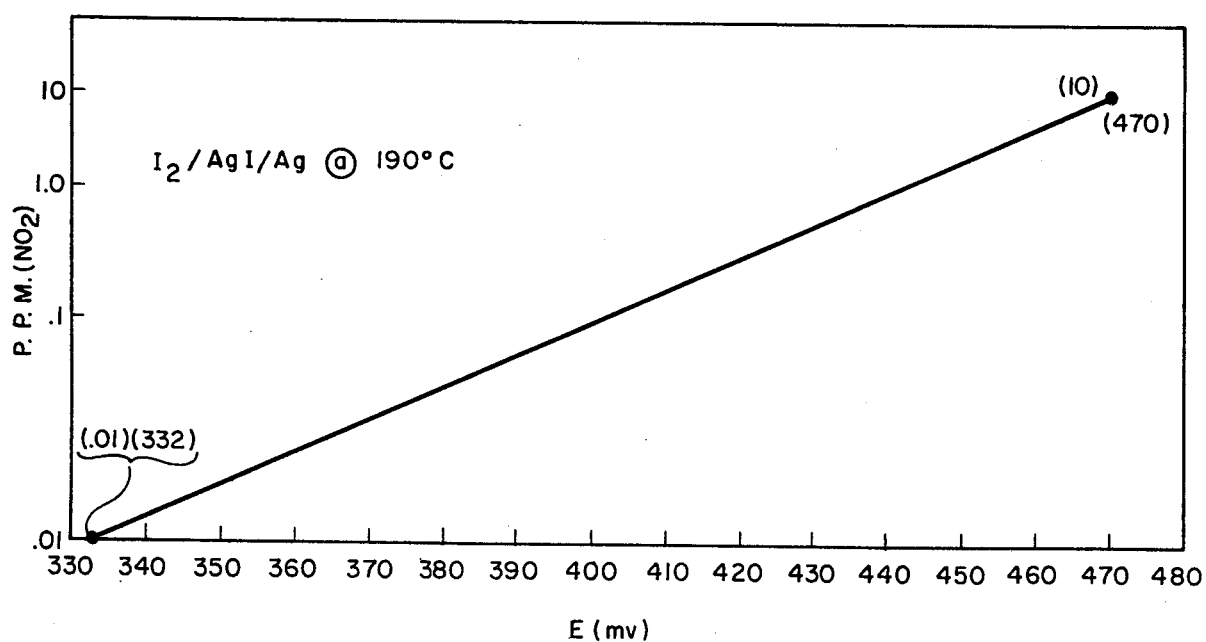
FIG. 2 is a typical calibration curve.

The foregoing device was placed in a controlled atmosphere and maintained at a temperature of about 190° C. A continuous stream of gas containing known concentrations of $NO_2$ was introduced into the device through inlet 16, and the potential across the electrodes monitored. Referring now to FIG. 2, therein is a typical plot of such a test. It is seen that the increase in potential varies exponentially in a uniform manner with the increase in concentration of $NO_2$, and that concentrations as low as 0.02 ppm are readily measurable with the device of the present invention. Further, when the tests are repeated on succeeding days, the measurements are substantially identical, whereas with the prior art devices such as disclosed in U.S. Pat. No. 3764,269, utilizing a current-measuring technique, a substantial decrease in current flow is obtained on succeeding days for a constant concentration. Thus, those devices require frequent calibration. In addition, it is found that for any given concentration of a component, that the response time of the device of the present invention is faster (by a factor of from about 1.2 to 2) than those constructed in accordance with the aforesaid patent.

It also has been found that minute amounts of halogen are liberated from lead iodide in the presence of light. The amount liberated is not enough to interfere with the accuracy of the device for concentration of $NO_2$ above about 0.2 ppm. However, at lower concentrations the lead iodide advantageously is shielded from light by placing it in an opaque container or the like.

It will be appreciated that the present invention should not be limited to the specific details of the particular embodiments described, since many modifications will be apparent to those skilled in the art. For example, the particular electrolyte and halogenic compound may be varied to produce a device capable of sensing a particular component of interest. Accordingly, the scope of the present invention should not be limited to the foregoing embodiments, rather the scope of the invention should be ascertained with reference to the following appended claims.

What is claimed is:

1. A device for sensing at least one component of a fluid substance comprising:
    (a) first means including a composition reactive with at least one component of said fluid to liberate elemental chlorine, bromine, fluorine or iodine upon exposure to said component;
    (b) a porous matrix electrode comprising a particulate layer of vitreous carbon having a median particle size of less than about 500 microns and in cooperative relation to said first means forming a first electrode through which said liberated chlorine, bromine, fluorine or iodine passes; and
    (c) a solid electrolyte cell with a voltage measuring means across its electrodes including said porous matrix electrode, said measuring means operatively associated with said matrix and responsive to said liberated chlorine, bromine, fluorine or iodine for measuring a voltage which is indicative of the concentration of said chlorine, bromine, fluorine or iodine, said concentration being a known fraction or multiple of the concentration of said component in said fluid.

2. The device of claim 1 wherein said vitreous carbon has a median particle size of from about 10 to 100 microns.

3. The device of claim 2 wherein said porous matrix electrode further includes a platinum screen in contact with said vitreous carbon.

4. The device of claim 3 wherein said iodine-containing composition is lead iodide.

5. The device of claim 1 wherein said composition is a chlorine-, bromine-, fluorine- or iodine-containing composition.

6. The device of claim 1 wherein said composition is an iodine-containing composition which is reactive in response to said at least one component of said fluid to liberate elemental iodine from said composition upon exposure to said component.

7. A device for sensing at least one component of a fluid substance comprising:
    (a) first means including at least one halogenic compound reactive in response to at least one component of said fluid to liberate an elemental halogen from said compound;
    (b) an electrochemical cell including a porous matrix electrode comprising a particulate layer of vitreous carbon having a median particle size of less than about 500 microns, operatively associated with said first means and adapted to respond to said liberated halogen, said cell including a solid ionic electrolyte body having one surface in contact with said porous electrode and another surface in contact with a silver-containing electrode; and
    (c) electrical means connected across said cell for measuring a voltage potential across said cell, said voltage potential being initiated by electrochemical response at the interface of said porous electrode and the electrolyte of the liberated halogen and being relatable in a known manner to the concentration of the detected component in said fluid.

8. The device of claim 7 wherein said at least one component is an oxidizing gas and said halogenic compound is reactive with said gas to liberate elemental chlorine, bromine, fluorine or iodine.

9. The device of claim 7 wherein said at least one component is a reducing gas and said halogenic compound is a chlorogenic, bromogenic or iodogenic compound reactive with said gas to liberate elemental chlorine, bromine or iodine.

10. The device of claim 7 wherein said at least one component is an acid gas and said halogenic compound is at least one chlorogenic, bromogenic or iodogenic compound reactive with said gas to liberate elemental chlorine, bromine or iodine.

11. The device of claim 7 wherein said at least one component is nitrogen dioxide and wherein said halogenic compound is lead iodide.

* * * * *